United States Patent
Stjernberg Bejhed et al.

(10) Patent No.: US 10,518,078 B2
(45) Date of Patent: Dec. 31, 2019

(54) COUPLING DEVICE

(71) Applicant: TADA MEDICAL AB, Stockholm (SE)

(72) Inventors: Rebecca Stjernberg Bejhed, Uppsala (SE); Katarina Hedbeck, Stockholm (SE); Christopher Blacker, Höllviken (SE); Hanna Andersson, Uppsala (SE); Ronny Brakhya, Huskvarna (SE); Robert Axelsson, Gränna (SE); Samuel Wikström, Jönköping (SE)

(73) Assignee: TADA MEDICAL AB (SE)

( * ) Notice: Subject to any disclaimer, the term of this patent is extended or adjusted under 35 U.S.C. 154(b) by 0 days.

(21) Appl. No.: 16/348,695

(22) PCT Filed: Nov. 8, 2017

(86) PCT No.: PCT/EP2017/078619
§ 371 (c)(1),
(2) Date: May 9, 2019

(87) PCT Pub. No.: WO2018/087153
PCT Pub. Date: May 17, 2018

(65) Prior Publication Data
US 2019/0275316 A1  Sep. 12, 2019

(30) Foreign Application Priority Data
Nov. 9, 2016 (SE) ..................... 1651467

(51) Int. Cl.
*A61M 39/26* (2006.01)
*A61M 39/10* (2006.01)
(Continued)

(52) U.S. Cl.
CPC ........ *A61M 39/26* (2013.01); *A61M 39/1011* (2013.01); *F16L 29/005* (2013.01);
(Continued)

(58) Field of Classification Search
CPC .. A61M 39/26; A61M 39/1011; A61M 39/18; A61M 2039/1016;
(Continued)

(56) References Cited

U.S. PATENT DOCUMENTS

| 5,492,147 A | 2/1996 | Challender et al. |
| 9,849,277 B2 | 12/2017 | Stroup et al. |

(Continued)

FOREIGN PATENT DOCUMENTS

| EP | 0 795 342 A2 | 9/1997 |
| EP | 2 298 407 A1 | 3/2011 |

(Continued)

OTHER PUBLICATIONS

WO 2013-153722, Cited in official Swedish Search Report dated Apr. 13, 2018 in related Swedish patent application No. 1751382-1.

(Continued)

*Primary Examiner* — Nathan R Price
*Assistant Examiner* — John A Doubrava
(74) *Attorney, Agent, or Firm* — Condo Roccia Koptiw LLP

(57) ABSTRACT

A coupling device (100) for transferring a fluid is provided. The coupling device comprises a first housing (110), a tube portion (140) projecting into the first housing, and a second housing (200) displaceably arranged within the first housing. The coupling device further comprises a third housing (300) releasably connectable to the second housing and displaceably arranged within the first housing when connected to the second housing. In a first position of the second housing, the first and second channels constitute a passage which is sealed by the first and second sealing elements when the second housing and the third housing are connected. In a second position, the tube portion projects through the first and second sealing elements and into the sealed passage for enabling a transfer of fluid through the coupling device.

15 Claims, 7 Drawing Sheets

(51) Int. Cl.
*F16L 29/00* (2006.01)
*F16L 37/28* (2006.01)
*A61M 39/18* (2006.01)

(52) U.S. Cl.
CPC .............. *F16L 37/28* (2013.01); *A61M 39/18* (2013.01); *A61M 2039/1016* (2013.01); *A61M 2039/1027* (2013.01); *A61M 2039/1072* (2013.01); *A61M 2039/263* (2013.01); *A61M 2039/267* (2013.01)

(58) Field of Classification Search
CPC .. A61M 2039/1027; A61M 2039/1072; A61M 2039/263; A61M 2039/267; F16L 29/005; F16L 37/28
USPC .................................................. 604/523, 256
See application file for complete search history.

(56) References Cited

U.S. PATENT DOCUMENTS

| | | | |
|---|---|---|---|
| 2003/0032940 A1 | 2/2003 | Doyle | |
| 2005/0090805 A1* | 4/2005 | Shaw | A61M 39/26 604/523 |
| 2006/0129109 A1* | 6/2006 | Shaw | A61M 39/26 604/246 |
| 2007/0169825 A1 | 7/2007 | Packham et al. | |
| 2012/0090712 A1 | 4/2012 | Bendt et al. | |
| 2013/0079730 A1 | 3/2013 | Mosler et al. | |
| 2015/0258324 A1 | 9/2015 | Chida et al. | |

FOREIGN PATENT DOCUMENTS

| | | |
|---|---|---|
| WO | WO 90/06151 A1 | 6/1990 |
| WO | WO 2006/043883 A1 | 4/2006 |
| WO | WO 2006/122406 A1 | 11/2006 |
| WO | WO 2012/152658 A1 | 11/2012 |
| WO | WO 2013/076667 A1 | 5/2013 |
| WO | 2013-153722 A1 | 10/2013 |
| WO | 2015-103499 A1 | 7/2015 |
| WO | 2016-147558 A1 | 9/2016 |
| WO | WO 2016/147558 A1 | 9/2016 |

OTHER PUBLICATIONS

WO 2016-147558, Cited in official Swedish Search Report dated Nov. 5, 2018 in related Swedish patent application No. 1651467-1.

* cited by examiner

COUPLING DEVICE

CROSS REFERENCE TO RELATED APPLICATIONS

This application is the National Stage Entry under 35 U.S.C. § 371 of Patent Cooperation Treaty Application No. PCT/EP2017/078619, filed 8 Nov. 2017, the contents of which are hereby incorporated by reference herein.

FIELD OF THE INVENTION

The present invention generally relates to the field of medical devices. More specifically, the present invention relates to a coupling device for transferring a fluid.

BACKGROUND OF THE INVENTION

During patient treatments, there may be a need of transferring one or more fluids (blood, blood products, one or more medicines, etc.) to and/or from a patient. As the fluid often is supplied via an element (e.g. a needle, cannula, catheter, trocar, or the like) inserted into the patient during treatments of this kind, it is desirable that the element remains relatively fixed after insertion into the patient. Involuntarily displacements and/or movements of the element after insertion into the patient may arise in case the patient or any medical staff accidentally pulls a tube connected to the element. Furthermore, stumbling accidents of the patient and/or medical staff over a tube connected to an element may also lead to element displacements. It will be appreciated that displacements of this kind of an element may not only be painful for the patient, but may also lead to consequences of the treatment if the transferring of fluid due to the element's displacement is not performed correctly. Furthermore, it should be noted that pulling an element inserted into a patient with force could damage the vessel of a patient. Furthermore, for a patient with a compromised immune system, a wounded vessel could lead to a serious infection.

In addition, in case of an accidental pulling of a tube for a transfer of a fluid to a patient, it is desirable that any leakage of the fluid is mitigated. For example, if the infusion liquid is toxic, any leakage from a broken tube may be especially hazardous.

SUMMARY OF THE INVENTION

It is an object of the present invention to mitigate one or more of the above problems and to provide a device for medical purposes which may conveniently mitigate effects of a tube exposed to forces, e.g. pulling forces, and in particular when the tube is connected to an element for transferring a fluid to/from a patient.

This and other objects are achieved by providing a coupling device having the features in the independent claim. Preferred embodiments are defined in the dependent claims.

Hence, according to the present invention, there is provided a coupling device for transferring a fluid. The coupling device comprises a first housing extending along a principal axis A. The first housing comprises a first opening at a back end portion thereof and a second opening at a front end portion thereof. Moreover, the coupling device comprises a tube portion extending from the first opening into the first housing. The coupling device further comprises a second housing which is displaceably arranged within the first housing along the principal axis between a first position at the front end portion of the first housing and a second position at the back end portion of the first housing. The second housing comprises a first sealing element. Furthermore, the coupling device comprises a third housing which is releasably connectable to the second housing and configured for displaceable arrangement within the first housing along the principal axis. The third housing comprises a channel through the third housing and a second sealing element arranged to seal the channel. In the first position of the second housing, the third housing is insertable into the first housing via the second opening thereof such that the first and second sealing elements are configured to abut each other and sealingly separate the tube portion and the channel. In the second position of the second housing, the third housing and the second housing are connected, and the tube portion projects through the first and second sealing elements for connection with the channel for enabling a transfer of fluid through the coupling device.

Thus, the present invention is based on the idea of providing a coupling device for transferring a fluid, wherein the coupling device may enable a transfer of fluid through the coupling device which is sealed to the outside environment when the coupling device is connected, and a leak-free interruption of a transfer of a fluid in case the coupling device is disconnected. More specifically, upon connection of the coupling device, first and second sealing elements firstly provide a sealing upon abutment with each other. Thereafter, a transfer of fluid is enabled by the tube portion of the coupling device, projecting through (penetrating) the first and second sealing elements. Upon disconnection of the coupling device, which disconnection may be triggered by a pulling force applied to the third housing and the second housing of the coupling device, the second housing may be displaced from its second (retracted) position to its first (extracted) position. Consequently, this results in a retraction of the tube portion from its position through the first and second sealing elements such that the second housing and the third housing subsequently become sealed again by the first and second sealing elements, respectively. In other words, the respective first and second sealing elements may conveniently stop a flow on either side of the respective sealing elements upon disconnection/detachment of the coupling device. Hence, the coupling device of the present invention may provide excellent sealing properties and avoid leakage, both during a transfer of fluid through the coupling device as well as during an interrupted flow of fluid through the coupling device as a result of a detachment or disconnection of the coupling device.

It will be appreciated that the ability of the coupling device to mitigate any leakage of fluid is advantageous for reasons of safety. For example, in case the coupling device is provided for a transfer of a toxic liquid, any leakage from the coupling device may be particularly hazardous. Hence, the coupling device of the present invention may significantly increase the safety of medical staff and/or patients.

Furthermore, the coupling device of the present invention is advantageous in that it may save fluid by its advantageous sealing properties. For example, in case the coupling device is used for a transfer of blood, the coupling device may mitigate any loss of blood and/or a contamination of the environment caused by a leakage in case of a detachment of the coupling device. Furthermore, by its excellent sealing properties, the coupling device may mitigate any contamination of the fluid (e.g. blood) transferred through the (connected) coupling device.

The present invention is further advantageous in that the coupling device provides a convenient detachment (disconnection) of the coupling device. For example, if the coupling device is connected to a tube for medical purposes, a pulling of the tube, e.g. by a patient and/or medical staff, may detach the third housing from the first and/or second housing of the coupling device, thereby mitigating any further pulling of the tube at the other end thereof. It will be appreciated that it may be desirable that (medical) tubes commonly used at hospitals, nursing homes, clinics, etc., are equipped with a coupling device of the present invention, as the coupling device may constitute a "weak link" of the tube. Hence, if a tube is connected between a patient and a source (e.g. an infusion pump or bag) and further comprises a coupling device according to the present invention, the coupling device may constitute the "weak link" of the tube where the tube may be "cut off" as a result of a pulling of the tube.

The coupling device is especially advantageous in case it is provided to a medical tube which in turn is connected to an element inserted into a patient for a transfer of fluid to and/or from the patient. This is realized as a displacement of the element may not only be painful for the patient, but may also lead to consequences of the patient's treatment if the transferring of fluid due to the element's displacement is not performed correctly. By the coupling device of the present invention, provided to a medical tube for medical purposes, it will be appreciated that equipment connected to the tube such as (infusion) elements, pumps and/or bags, etc., may be spared from damage caused by a pulling of the medical tube.

By the coupling device of the present invention, provided to a medical tube, it will be appreciated that equipment connected to the medical tube such as (infusion) elements, pumps and/or bags, etc., may be spared from damage caused by a pulling of the medical tube.

The coupling device of the present invention is further advantageous in that consequences related to medical staff and/or patients tripping and/or falling over (a) medical tube(s) comprising one or more coupling devices may be mitigated.

The coupling device of the present invention is further advantageous in that it is easily, conveniently and efficiently (re)connected if detached or disconnected. For example, in case a medical tube comprising a coupling device according to the present invention is pulled apart, it may be desirable to be able to reinstate the (infusion) therapy again as quickly as possible. The coupling device meets this demand, as the (re)connection of the coupling device may be performed quickly and intuitively due to the innovative configuration of the coupling device.

The coupling device of the present invention is further advantageous in that its components (e.g. the first, second and/or third housing, the first and second sealing elements, etc.) are designed to have relatively smooth outer surfaces, such that they may be cleaned and/or disinfected in an easy and efficient manner. For example, after a cleaning and/or disinfection of a dissembled coupling device, the respective components of the coupling device may subsequently be reassembled into the coupling device.

The coupling device of the present invention is further advantageous in that it is relatively inexpensive to manufacture and is easily assembled. Consequently, the coupling device may primarily be designed for single-use, i.e. the coupling device may for example be used for one patient and one therapy (e.g. infusion).

The coupling device of the present invention is further advantageous in that its design minimizes dead space of the fluid path through the coupling device, thereby mitigating the occurrence of infectious agents. Furthermore, the inventive design of the coupling device mitigates leakage of the fluid.

The coupling device of the present invention is further advantageous in that the flow of fluid through the coupling device is linear along the principal axis of the coupling device. In other words, the design of the coupling device may hereby avoid an undesired turbulence of the fluid during operation of the coupling device.

By the term "displaceably arranged", it is here meant that the second housing and the third housing may be arranged or mounted within the first housing in such a way that they are displaceable or moveable within the first housing.

By the term "displaceable arrangement", it is here meant that the third housing may be arranged or mounted within the first housing in such a way that the third housing is displaceable or moveable within the first housing.

By the term "releasably connectable", it is here meant that the second housing and the third housing are configured to be attached and detached by applying a respective force.

By the term "sealingly separate", it is here meant that the first sealing element and the second sealing element separate the tube portion and the channel in a sealing manner, such that no fluid can pass between the tube portion and the channel.

According to an embodiment of the present invention, the coupling device further comprises a locking arrangement. In the second position, the second housing is releasably connected to the first housing via the locking arrangement. In other words, when the second housing is in its second, refracted position in the first housing, the second housing may be releasably connected to the first housing. It will be appreciated that this position of the second housing implies an enabled transfer of fluid through the coupling device, and the present embodiment is advantageous in that a fluid may be transferred through the device in a stationary state of the coupling device, i.e. without the need of applying any pressure on one or more components of the coupling device.

According to an embodiment of the present invention, whereby in case of a force F applied on the third housing connected to the second housing in the second position along the principal axis towards the first position exceeds a predetermined threshold, the second housing is configured to be released from a connection to the first housing in the second position, the second housing is configured to be displaced from the second position into the first position, and the third housing is configured to be released from the connection to the second housing. Hence, in case of a (pulling) force applied on the third housing (or between the third housing and the second housing) exceeds a predetermined threshold, the third housing is configured to detach (disconnect) from the second housing according to the disclosed arrangement. The present embodiment is advantageous in that the third housing and the second housing of the coupling device are only configured to detach in case the coupling device is subjected to a pulling force applied to the third housing which exceeds a predetermined threshold value, such that the transfer of fluid through the coupling device is interrupted. In other words, the third and second housing are only configured to separate from each other when exposed to a pulling force which is relatively strong. Hence, the third and second housing of the coupling device are configured to stay connected in case the coupling device is subjected to a relatively weak force which does not exceed the predetermined threshold value, such that the coupling device may remain operative for transferring a fluid.

In case there is provided a tube for medical purposes equipped with a coupling device of the present invention, it will be appreciated that the coupling device is further advantageous in that the coupling device may be detached before any relatively large force, subjected to a portion of the tube on one side of the coupling device, is transferred to the other portion of the tube, on the other side of the coupling device. For example, if an element is connected to the tube, the coupling device may mitigate any pull, jerk, twitch or the like, of the element.

The coupling device of the present invention is further advantageous in that consequences related to medical staff and/or patients tripping and/or falling over tubes comprising one or more coupling devices may be mitigated.

The embodiment is advantageous in that the threshold of the force F can be conveniently set or determined according to the purpose of the coupling device. For example, in case a coupling device is used when a needle is inserted into a patient, the threshold of the force F can be determined to be relatively low. In contrast, in case a coupling device is used when a urinary catheter is used, the threshold of the force F can be determined to be relatively high.

According to an embodiment of the present invention, the coupling device comprises a locking mechanism for releasable connection of the third housing to the second housing. The embodiment is advantageous in that the third housing may be conveniently connected to (or disconnected from) the second housing by means of the locking element(s).

According to an embodiment of the present invention, in the second position of the second housing, the third housing and the second housing are connected by the locking mechanism. Hence, in the second, retracted position of the second housing, when the tube portion projects through the first and second sealing elements and into the passage for enabling a transfer of fluid through the coupling device, the locking mechanism connects the second and third housings to each other. The embodiment is advantageous in that the locking mechanism may provide a reliable connection of the second and third housings to each other, such that the second and third housings provide a sealed (leak-proof) transfer of fluid through the coupling device.

According to an embodiment of the present invention, the third housing comprises a first locking element of the locking mechanism, and the second housing comprises a second locking element of the locking mechanism, wherein the first and second locking elements are configured to releasably lock upon rotation of the first and second locking elements with respect to each other. For example, the locking mechanism for connecting the second and third housings according to the present or to any previously disclosed embodiment may comprise a connection of a male-female type. It will be appreciated that the locking mechanism of a male-female type may comprise at least one groove and at least one projection configured to project into the at least one groove.

According to an embodiment of the present invention, during a displacement of the second housing and third housing from the first position to the second position, the second locking element is configured to rotate with respect to the first locking element for mating engagement with the first locking element such that the third housing and the second housing are connected in the second position, and during a displacement of the second housing and third housing from the second position to the first position, the second locking element is configured to rotate with respect to the first locking element for disengaging the mating engagement such that the third housing and the second housing are disconnected in the first, extracted position. In other words, when the second and third housing are pushed into the first housing of the coupling device from the first to the second position, the second and third housings connect via a rotation of the first and second locking elements with respect to each other. Analogously, when the second and third housing are pulled out of the first housing of the coupling device from the second to the first position, the second and third housings disconnect via a rotation of the first and second locking elements with respect to each other According to an embodiment of the present invention, at least one of the first and second sealing elements comprises a resilient membrane. It will be appreciated that the resilient membrane(s) is (are) configured to become arranged (clamped) between the first and second sealing elements upon connection of the second and third housings. The embodiment is advantageous in that the sealing element(s) may provide an efficient sealing between the second and third housings via the resilient membrane(s) when the second and third housings are connected, such that any leakage between the second and third housings can be avoided.

According to an embodiment of the present invention, the at least one resilient membrane has a convex shape and is configured to flatten upon abutment of the first sealing element with the second sealing element. In case each of the first and second sealing elements comprises a resilient, convex-shaped membrane, it will be appreciated that the membranes may push away air and form an air-tight seal, furthermore minimizing dead space, when the membranes are pressed against each other. Hence, the present embodiment may even further improve the sealing properties of the coupling device.

According to an embodiment of the present invention, the resilient membrane comprises silicone. The embodiment is advantageous in that silicone is particularly suitable for sealing purposes, thereby even further improving the sealing of the coupling device. Furthermore, the use of silicone of the membrane is advantageous in that the tube portion may penetrate the membrane without (or at least minimizing a) tearing of the material, such that an undesired wear of the membrane and/or a contamination of the fluid in the flow of fluid through the coupling device may be avoided.

According to an embodiment of the present invention, the at least one resilient membrane comprises a through hole, and wherein the at least one resilient membrane is configured to be arranged into a respective fitting of the first and/or second sealing element, the size of the at least one resilient membrane being larger than the fitting such that the through hole is configured to be compressed upon arrangement of the at least one resilient membrane into the fitting. The embodiment is advantageous in that the tube portion may be guided by the compressed through hole upon projection of the tube portion through the sealing elements. The embodiment is further advantageous in that the compressed through hole may avoid, or at least minimize, a tearing of the membrane material upon penetration of the tube portion through the sealing elements.

According to an embodiment of the present invention, the coupling device further comprises an alarm arrangement configured to generate an alarm in case the second housing and the third housing are disconnected. The present embodiment is advantageous in that the alarm arrangement may quickly and efficiently alert a patient, medical staff and/or other persons that the second and third housings of the coupling device have been disconnected or detached, and that the fluid transportation through the coupling device (and, in case the coupling device is provided to a medical tube, also through the medical tube) has been interrupted.

According to an embodiment of the present invention, the alarm comprises at least one of a visual alarm and an audible alarm. The present embodiment is especially advantageous when considering that patients often may suffer from impaired eye sight and/or impaired hearing. The present embodiment is further advantageous in that the alarm may alert medical staff which is not present in the same room as the patient.

According to an embodiment of the present invention, the coupling device is configured to generate a tactile feedback to an operator when the second housing is in the second position. By the term "tactile feedback", it is here meant a physical sensation, alert, or the like, which can be felt by an operator upon handling of the coupling device. For example, the coupling device may be configured to generate a tactile feedback to an operator when the second housing, in its second position, becomes connected to the first housing. The present embodiment is advantageous in that an operator may be assured that the coupling device is correctly coupled or connected when the second housing is in the second, retracted position, as the coupling device hereby is configured to enable a transfer of liquid through the coupling device.

According to an embodiment of the present invention, there is provided a medical tube for transferring a fluid to or from a patient, wherein the medical tube comprises at least one coupling device according to any one of the preceding embodiments. In other words, the medical tube may comprise a first tube portion and a second tube portion, wherein a coupling device may be arranged between the first and second tube portions. By the term "medical tube" it is here meant substantially any tube for medical purposes, e.g. an infusion tube or urinary catheter. The present embodiment is advantageous in that the medical tube may be conveniently disconnected or detached via the coupling device. For example, a pulling of the medical tube, e.g. by a patient and/or medical staff, may detach the third housing from the second housing of the coupling device, thereby mitigating any further pulling of the tube at the other end thereof. Hence, the medical tube may comprise a "weak link" by means of the coupling device, which is particularly advantageous for medical tubes used at hospitals, nursing homes, clinics, etc.

According to an embodiment of the present invention, there is provided a medical kit comprising at least one medical tube according to the previous embodiment. The at least one medical tube comprises at least one coupling arrangement provided at at least one end thereof, and at least one element connected to the medical tube via the at least one coupling arrangement. It will be appreciated that the coupling arrangement may be of substantially any type, e.g. a standardized coupling which may be possible to couple to many different kinds of elements. For example, the (medical) element(s) may be an element arranged for insertion into a patient and configured to transfer a fluid into, or out from, a patient, such as a needle, cannula, catheter, trocar, or the like. Alternatively, or in addition, the element(s) may be at least one container arranged to supply a fluid to/from a patient via the medical tube. The present embodiment is advantageous in that the medical kit may increase the safety during a medical process, e.g. an infusion process. More specifically, the medical kit may conveniently mitigate effects of a medical tube exposed to forces, e.g. by a pulling of the medical tube by the patient and/or medical staff, and in particular when the medical tube is connected to an element for transferring a fluid to and/or from a patient.

Further objectives of, features of, and advantages with, the present invention will become apparent when studying the following detailed disclosure, the drawings and the appended claims. Those skilled in the art will realize that different features of the present invention can be combined to create embodiments other than those described in the following.

BRIEF DESCRIPTION OF THE DRAWINGS

This and other aspects of the present invention will now be described in more detail, with reference to the appended drawings showing embodiment(s) of the invention.

DETAILED DESCRIPTION

Figure 1A:
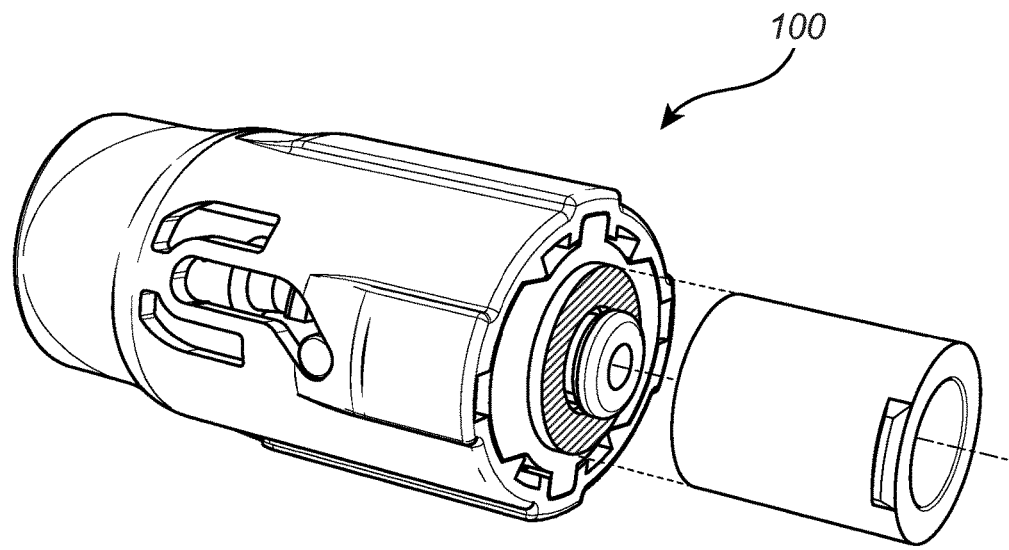
FIGS. 1a-b are schematic views of a coupling device according to an exemplifying embodiment of the present invention.
Figure 1B:
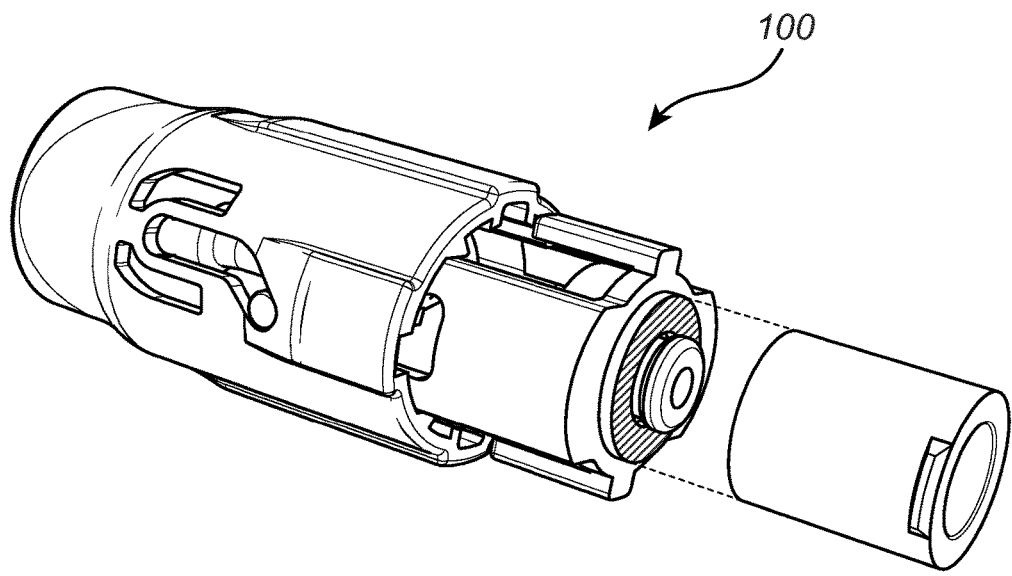

FIGS. 1a-b are schematic views of a coupling device 100 according to an exemplifying embodiment of the present invention. It will be appreciated that FIGS. 1a-b are provided for an initial description of the coupling device 100, and that a more detailed description of the properties and operation of the coupling device 100 is provided in the following figures and associated text.

The coupling device 100 is provided for the transfer of a fluid P through the coupling device 100 when the coupling device 100 is in its connected state. In FIG. 1a, a connection of the coupling device 100 has been initiated, which will be described in more detail in the following text and associated figures. In FIG. 1b, a disconnection of the coupling device 100 has been initiated. Eventually, the coupling device 100 becomes disconnected (detached), whereby the transfer of fluid through the coupling device 100 is interrupted.

FIGS. 2a-d are schematic, cross-sectional views of a coupling device 100 according to an exemplifying embodiment of the present invention. It will be appreciated that the four FIGS. 2a-d disclose exemplifying and momentary positions of a connection of a coupling device 100 for an increased understanding of the operation of the coupling device 100. Hence, an analogous disconnection of the coupling device 100 may be anticipated by the reverse order of the figures, and is therefore not presented in more detail.

Figure 2A:
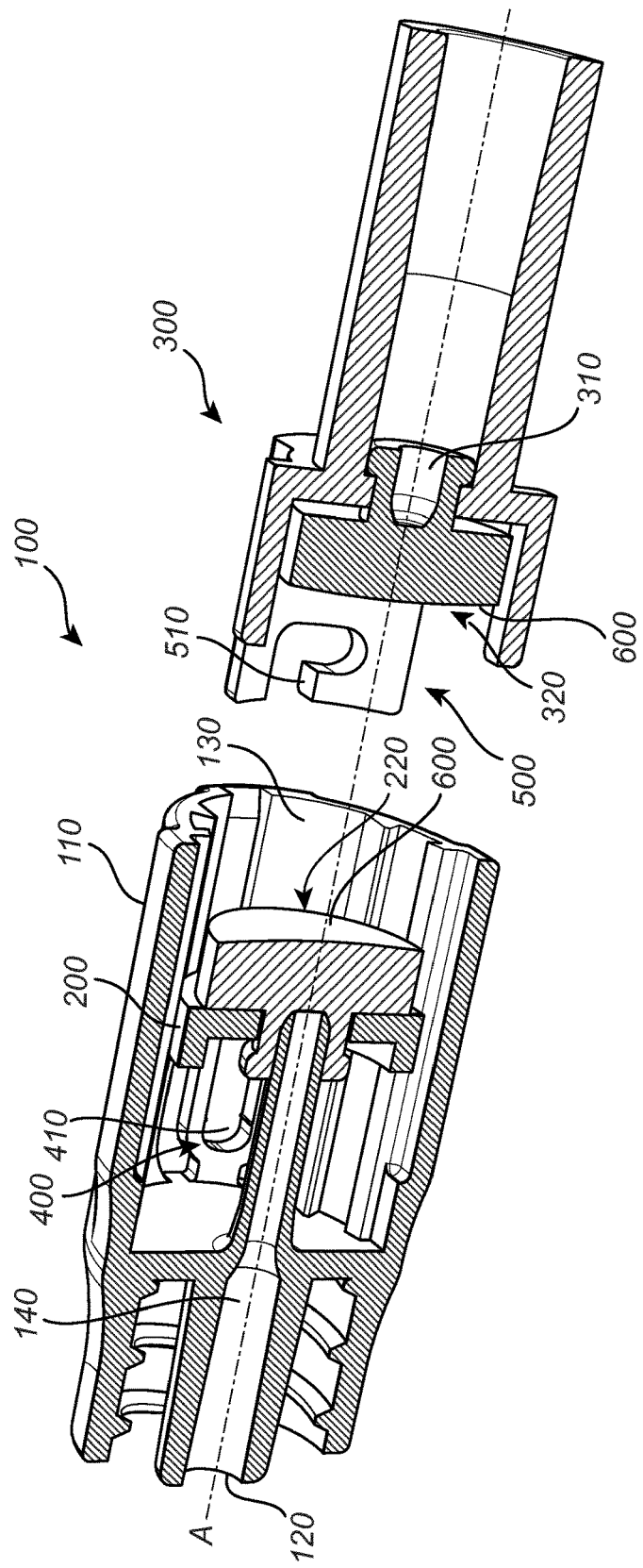
FIGS. 2a-d are schematic, cross-sectional views of a coupling device according to an exemplifying embodiment of the present invention, FIGS. 3a-b schematically shows locking and unlocking operations of a coupling device according to exemplifying embodiments of the present invention, FIG. 4 schematically shows a disconnection of the coupling device.

FIG. 2a is a schematic view of a coupling device 100 for transferring a fluid, wherein the coupling device 100 is shown in a disconnected state. The coupling device 100 comprises a cylinder-shaped first housing 110 with an elliptic cross-section, wherein the first housing 110 extends along a principal axis A. The first housing 110 comprises a first opening 120 at a central portion of the back end portion (e.g. a bottom part) of the first housing 110, and a second opening 130 at the front end portion of the first housing 110. The coupling device 100 further comprises a tube portion 140 which extends from the first opening 120 of the first housing 110 into the interior of the first housing 110. The end of the tube portion 140 which point towards the interior of the first housing 110 may be formed to be sharp or pointed, and the end of the tube portion 140 exemplified in FIG. 2a is beveled. However, the end of the tube portion 140 may alternatively be straight, i.e. without any sharp or pointed end.

The coupling device 100 further comprises a second housing 200 which is enclosed by the first housing 110 and is displaceably arranged within the first housing 110 along the principal axis A. It will be appreciated that the second housing 200 may be fittingly arranged within the first housing 110, e.g. by means of grooves or the like. In FIG. 2a, the second housing 200 is positioned in a first (extracted) position within the first housing 110. For example, the first, extracted position may constitute a position towards (or at) the front end portion of the first housing 110. The second housing 200 comprises a first sealing element 220, which is exemplified as a cushion or pad-like element arranged at an end of the tube portion 140 of the first housing 110.

The coupling device 100 further comprises a third housing 300 which in the disconnected state of the coupling device 100 is separate from the first housing 110 and second housing 200 of the coupling device 100. The third housing 300 comprises a channel 310 which is arranged through the third housing 300. The third housing 300 further comprises a second sealing element 320 which is arranged to seal the second channel 310.

It will be appreciated that in the disconnected state of the coupling device 100 as shown in FIG. 1a, there can be no passage of fluid through the coupling device 100. More specifically, the first sealing element 220 of the second housing 200 seals the tube portion 140 such that there is no passage of fluid through the second housing 200 or first housing 110. Analogously, the second sealing element 320 seals the second channel 310 such that there is no passage of fluid through the third housing 300.

The first sealing element 220 and/or the second sealing element 320 may comprise, or consist of, a respective resilient membrane 600 for sealing purposes. The membrane 600 may comprise or consist of substantially any material which is suitable for sealing purposes, e.g. silicone. Furthermore, the first sealing element 220 and/or second sealing element 320 may have a convex shape. According to an alternative embodiment, the resilient membrane(s) 600 may comprise a through hole, and the resilient membrane(s) 600 may be configured to be arranged into (a) fitting(s) of the first 220 and/or second 320 sealing element (not shown). The size of the resilient membrane(s) 600 may hereby be larger than the fitting(s) such that the through hole(s) is (are) configured to be compressed upon arrangement of the resilient membrane(s) 600 into the fitting.

The third housing 300 is insertable into the first housing 110 via the second opening 130 of the first housing 110. Hence, the first housing 110 is able to receive the third housing 300 via the second opening 130 thereof and accommodate the third housing 300 within the first housing 110. The first housing 110 and the third housing 300 may have elliptic cross-sections, whereas the second housing 200 may have a circular cross-section. It will be appreciated that the provision of elliptic cross-sections may facilitate the coupling between the housings. For example, the third housing 300 may be connected to the second housing 200 by a relative arrangement of 0° or 180° between the third housing 300 and the second housing 200.

In the exemplifying embodiment of the coupling device 100 in FIG. 2a, the coupling device 100 comprises a locking mechanism 500 for releasable connection of the third housing 300 to the second housing 200. The third housing 300 comprises a first locking element 510 of the locking mechanism 500, wherein the first locking element 510 has the form of one or more hooks projecting from the third housing 300. The second housing 200 comprises a second locking element (not shown) of the locking mechanism 500 for locking engagement with the first locking element 510 of the locking mechanism 500.

The coupling device 100 further comprises a locking arrangement 400 for releasably locking and/or connecting the second housing 200 to the first housing 110. The locking arrangement 400 comprises at least one groove 410 in the first housing 110 into which a locking element of the second housing 200 is configured to matingly engage (shown in FIG. 3a). The locking arrangement 400 of the coupling device 100 may be configured to generate a tactile feedback to an operator when the second housing 200 is in the second position. For example, the locking arrangement 400 may be configured to generate a snap and/or click sensation upon locking, such that an operator may be informed or made aware that the second housing 200 is connected to the first housing 110 in the second position.

Figure 2B:
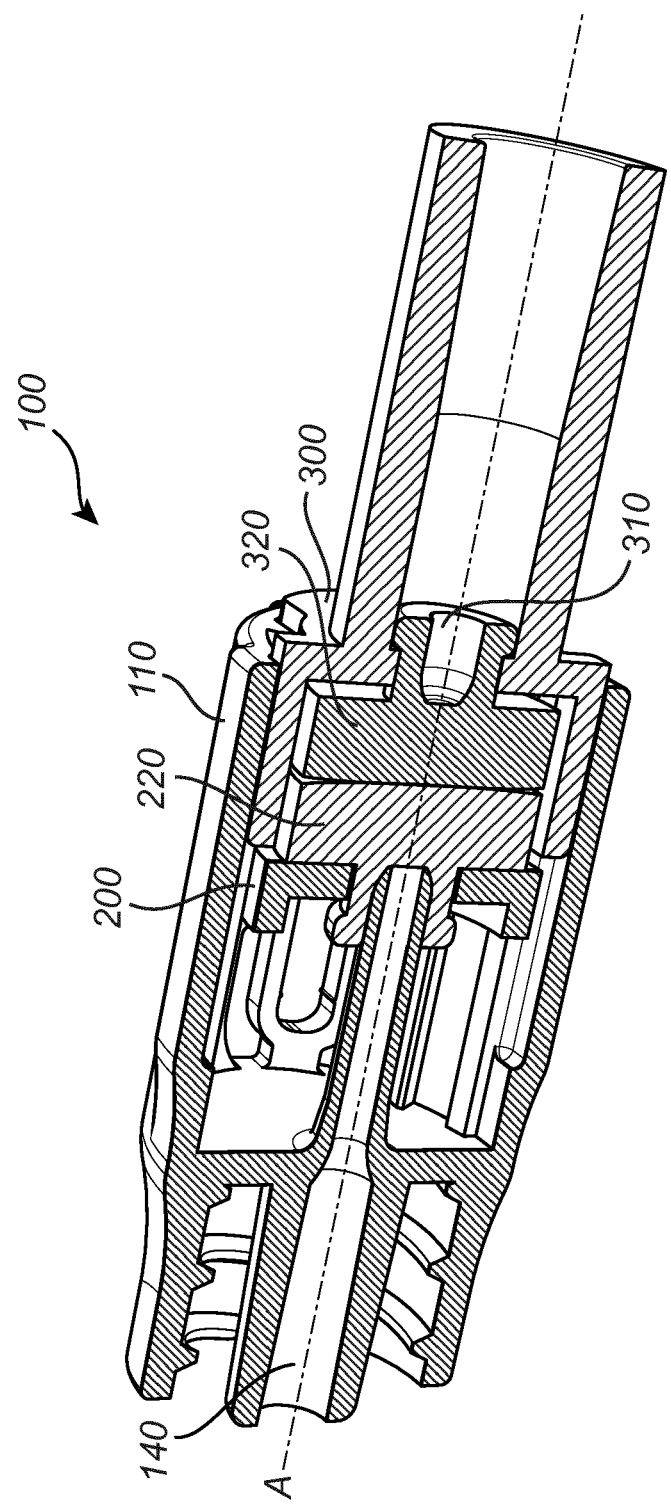

FIG. 2b is a schematic view of a coupling device 100 for transferring a fluid, wherein the third housing 300 has been inserted in the first housing 110 via its second opening 130 and along the principal axis A, as compared to FIG. 2a. Furthermore, in this state or position of the coupling device 100, the first sealing element 220 of the second housing 200 and the second sealing element 320 of the third housing 300 abut. Here, both the first sealing element 220 and the second sealing element 320 comprise resilient membranes 600 of convex shape, such that the central portions of the respective elements are initially configured to come into contact upon insertion of the third housing 300 into the first housing 110. In this embodiment, the convex-shaped membranes of the first and second sealing elements 220, 320 are configured to flatten upon abutment of the first sealing element 220 with the second sealing element 320. In this manner, the first and second sealing elements 230, 320 may sealingly separate the tube portion 140 of the first housing 110 and the channel 310 of the third housing 300.

Figure 2C:
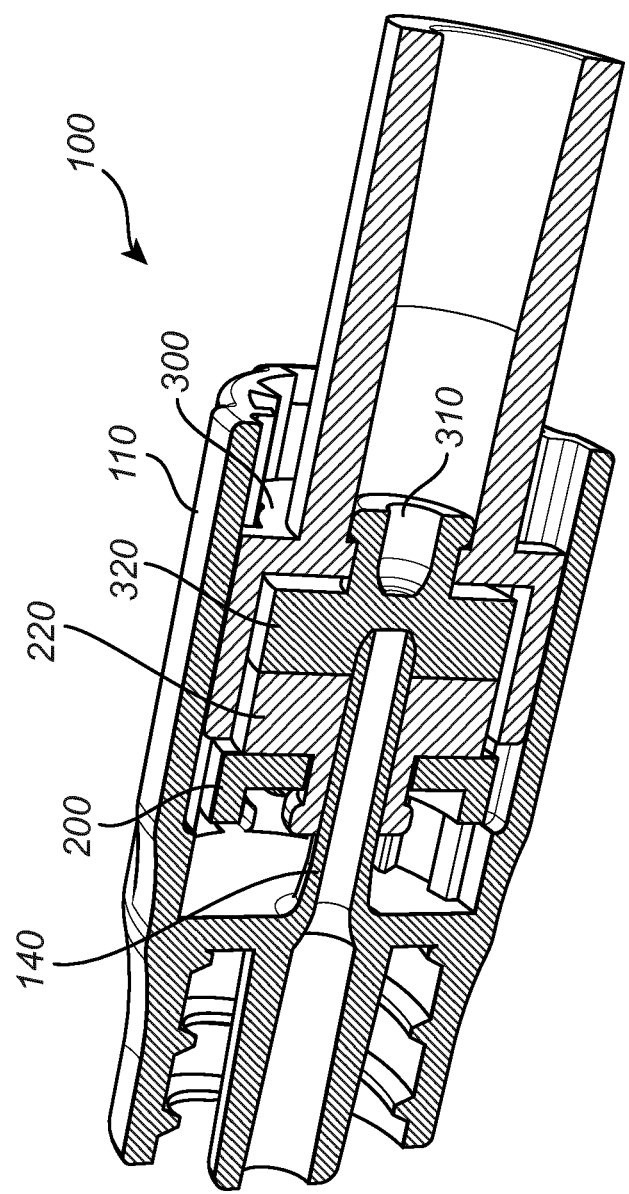

FIG. 2c is a schematic view of a coupling device 100 for transferring a fluid, wherein the second housing 200 and the third housing 300 are being displaced within the first housing 110. In this depicted current state of the coupling device 100, the convex-shaped membranes of the first and second sealing elements 220, 320 have flattened as a consequence of the force between the first sealing element 220 with the second sealing element 330, and the original shapes of the convex membranes are schematically indicated. During the movement of the second housing 200 (and the third housing 300) from the first, extracted position to the second, retracted position of the second housing, the tube portion 140 of the first housing 110 gradually projects through the first sealing element 220 and the second sealing element 320 for connection with the channel 310 for enabling a transfer of fluid through the coupling device 100. Furthermore, during this movement, the third housing 300 and the second housing 200 are configured to engagingly and releasably lock via the locking mechanism upon rotation of the first locking element and the second locking element with respect to each other.

Figure 2D:
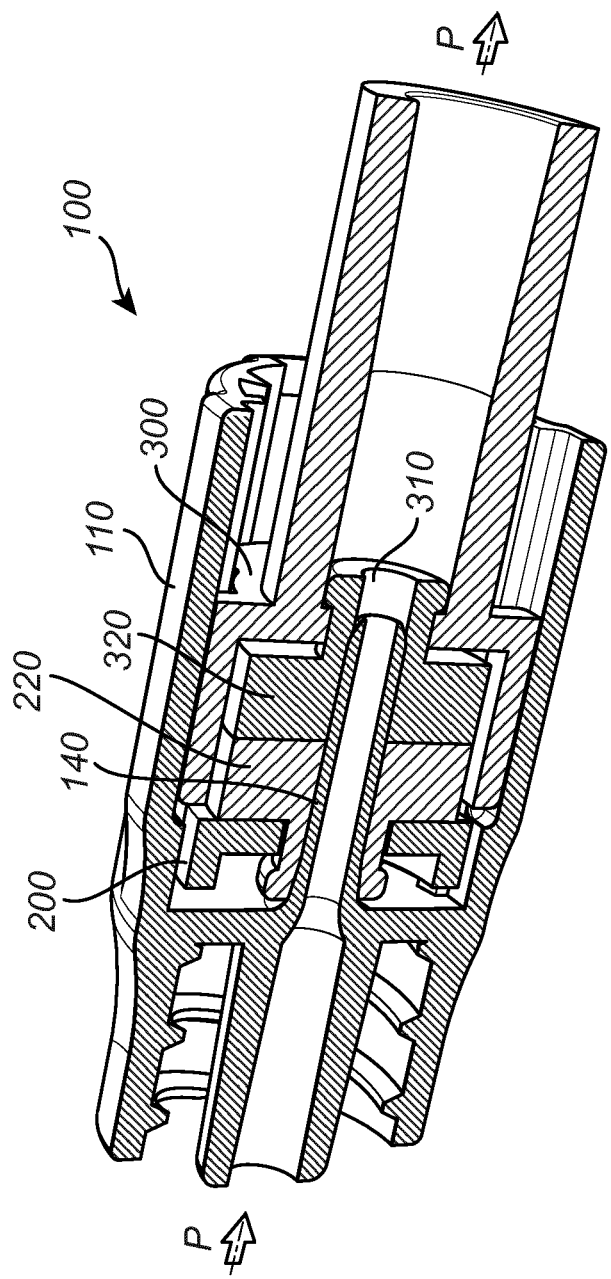

FIG. 2d is a schematic view of a coupling device 100 for transferring a fluid, wherein the second housing 200 is positioned in the second position in the first housing 110, and the third housing 300 is connected to the second housing 200. In this position, the third housing 300 and the second housing 200 are connected by means of the locking mechanism (not shown). The tube portion 140 projects or penetrates through the first sealing element 220 and the second sealing element 320. Furthermore, the tube portion 140 becomes fittingly inserted and debouches into the channel 310 of the third housing 300. In this configuration of the coupling device 100, a transfer of fluid through the coupling device 100 is enabled.

Figure 3A:
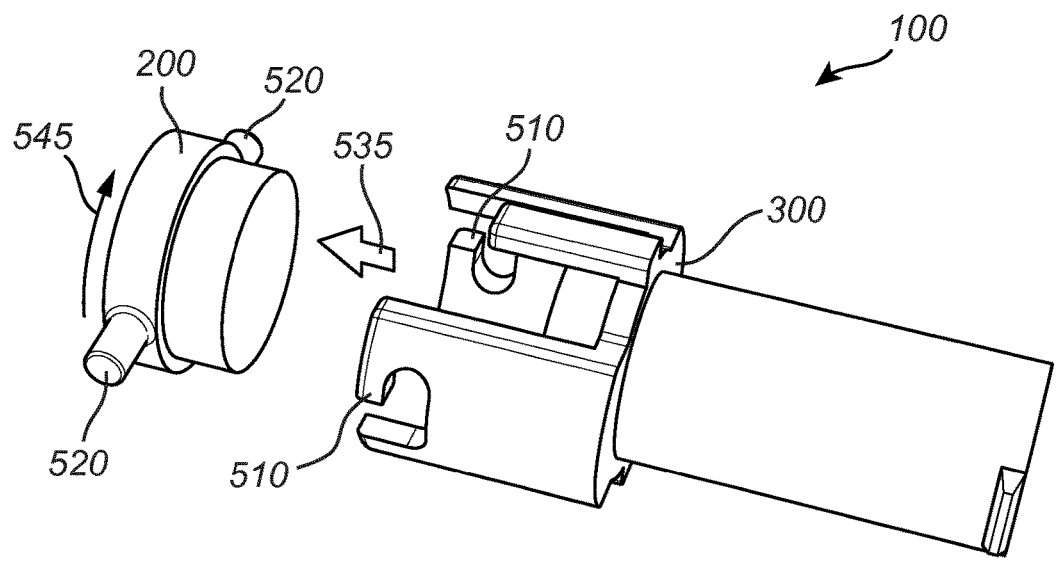

FIG. 3a schematically shows a simplified view of a portion of the coupling device 100 as previously described. Here, the second housing 200 and the third housing 300 have been extracted from the coupling device for reasons of understanding of the locking operation of the second housing 200 and the third housing 300. The locking mechanism in FIG. 3a comprises a first locking element 510 of the third housing 300, wherein the first locking element 510 comprises two projecting portions each comprising a groove. The locking mechanism in FIG. 3a further comprises a second locking element 520 of the second housing 200, wherein the second locking element 520 comprises two projections. Upon movement of the third housing 300 towards the second housing 200, as indicated by arrow 535, the second locking element 520 is configured to rotate, as indicated by arrow 545, as the result of the second locking element 520 being guided by a groove in the first housing (not shown). The second locking element 520 is hereby rotated with respect to the first locking element 510 for mating engagement with the first locking element 510 such that the third housing 300 and the second housing 200 become connected in the second position of the second housing 200. It will be appreciated that second housing 200, in the second position, is releasably connected to the first housing 110 via the at least one groove 410 (see FIG. 2a) and the second locking element 520.

Figure 3B:
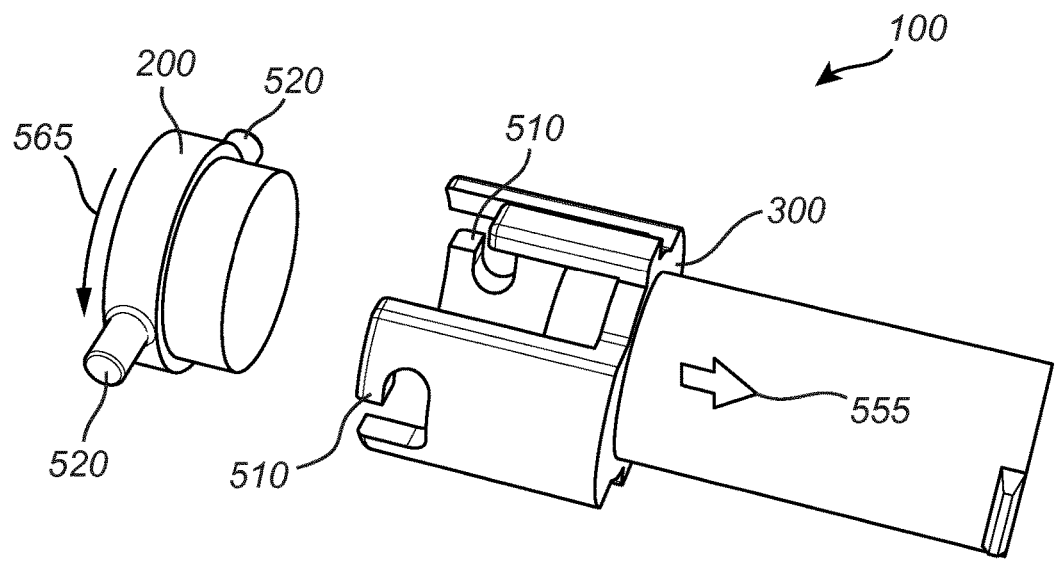

Analogously, FIG. 3b schematically shows a simplified view of a portion of the coupling device 100 as previously described, and furthermore shows an unlocking operation of the second housing 200 and the third housing 300 of the coupling device 100 in a schematic manner. During a displacement of the second housing 200 and the third housing 300 from the second, retracted position to the first, extracted position, as indicated by arrow 555, the second locking element 520 is configured to rotate, as indicated by arrow 565, with respect to the first locking element 510. As a result, the second locking element 520 disengages the mating engagement with the third housing 300. The second locking element 520 is hereby rotated with respect to the first locking element 510 such that the third housing 300 and the second housing 200 become disconnected in the first position of the second housing 200.

Figure 4:
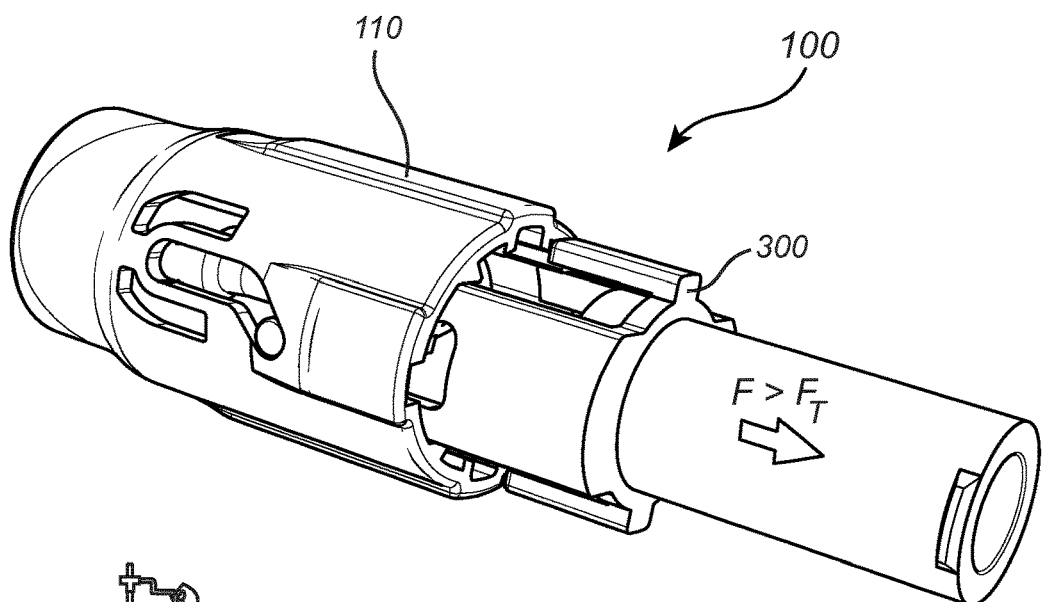

FIG. 4 schematically shows a disconnection of the coupling device 100 in case of a force F applied on the third housing 300 along the principal axis A exceeds a predetermined threshold. FT. In this case, the second housing (not shown) is configured to be released from a connection to the first housing 110 when the second housing is in its second, retracted position. Thereafter, the second housing and the third housing 300 are configured to be displaced from the second position into the first position, and the third housing 300 is configured to be released from its connection to the second housing. Eventually, the coupling device 100 becomes disconnected (detached), whereby the transfer of fluid through the coupling device 100 is interrupted.

It will be appreciated that the coupling device 100 furthermore may comprise an alarm arrangement (not shown). The alarm arrangement may be configured to generate an alarm in case the second housing 200 and the third housing 300 are disconnected. The alarm may for example comprise a visual alarm and/or an audible alarm. Furthermore, the alarm may be coupled (wirelessly or by wire) to any other equipment used by the medical staff for monitoring the patient(s).

Figure 5:
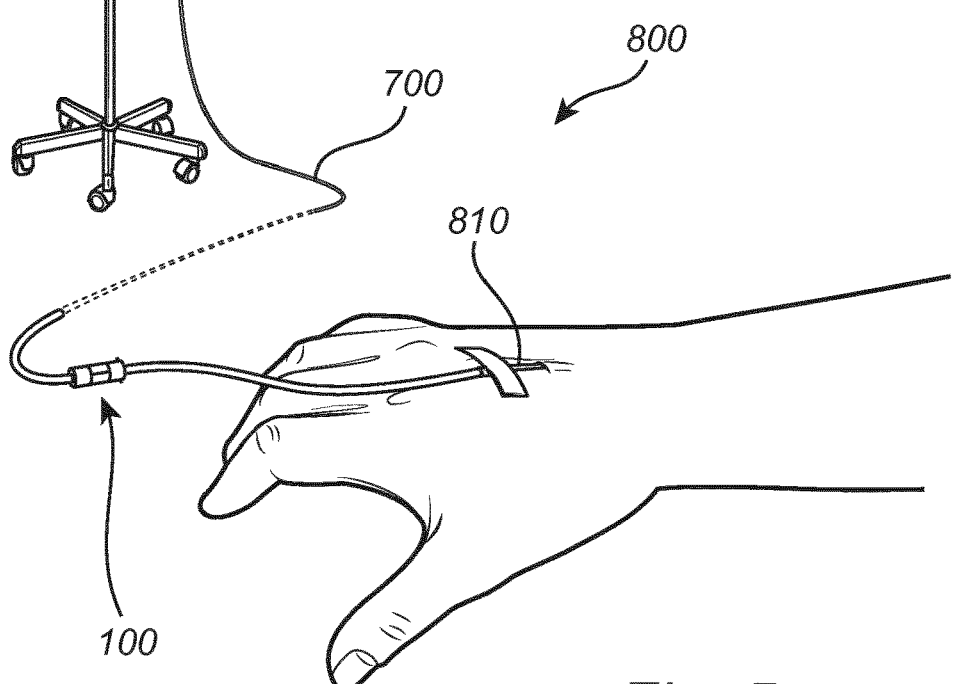
FIG. 5 shows a schematic view of a medical kit according to an embodiment of the present invention.

FIG. 5 shows a medical kit 800 according to an embodiment of the present invention. The medical kit 800 comprises a medical (e.g. infusion) tube 700, which in turn comprises a schematically indicated coupling device 100. One or more elements may be connected to the medical tube via coupling arrangement(s) provided at end portions of the medical tube 700, wherein the coupling arrangement(s) may be of standardized type for coupling to different kinds of elements. For example, and as shown in FIG. 5, an element 810 is connected to an end portion of the medical tube 700, wherein the element 810 is arranged for insertion into a patient and configured to transfer a fluid to and/or from a patient. Furthermore, at the other end of the medical tube 700, the medical tube 700 is coupled to a container 820 (e.g. an infusion bag) arranged to supply a (infusion) fluid to a patient via the medical tube 700 and the element 810. It will be appreciated that the medical tube 700 may comprise a plurality of coupling devices 100 although FIG. 5 merely shows the use of one coupling device 100 for reasons of simplicity. The coupling device 100 may furthermore comprise at least one coupling arrangement, e.g. arranged at one or both ends of the coupling device 100, for coupling to different kinds of elements. Furthermore, the coupling arrangement(s) may be of substantially any type, e.g. a standardized coupling which may be possible to couple to many different kinds of elements. For example, the coupling arrangement(s) may comprise a coupling of Luer lock type and/or Luer slip type.

The person skilled in the art realizes that the present invention by no means is limited to the preferred embodiments described above. On the contrary, many modifications and variations are possible within the scope of the appended claims. For example, it will be appreciated that the figures are merely schematic views of a coupling device 100 according to embodiments of the present invention. Hence, any elements/components of the coupling device may have different dimensions, shapes and/or sizes than those depicted and/or described.

The invention claimed is:

1. A coupling device for transferring a fluid, the coupling device comprising:
 a first housing extending along a principal axis, the first housing comprising a first opening at a back end portion thereof, a second opening at a front end portion thereof, and a tube portion extending from the first opening into the first housing;
 a second housing displaceably arranged within the first housing along the principal axis between a first position at the front end portion of the first housing and a second position at the back end portion of the first housing, the second housing comprising a first sealing element; and
 a third housing releasably connectable to the second housing and configured for displaceable arrangement within the first housing along the principal axis, the third housing comprising a channel through the third housing, and a second sealing element arranged to seal the channel,
 whereby, in the first position of the second housing, the third housing is insertable into the first housing via the second opening thereof, and insertable between the first housing and the first sealing element, such that the first and second sealing elements are configured to abut each other and sealingly separate the tube portion and the channel, and whereby, in the second position of the second housing, the third housing and the second housing are connected and the tube portion projects through the first and second sealing elements for connection with the channel such that a transfer of fluid through the coupling device is enabled.

2. The coupling device according to claim 1, further comprising a locking arrangement, whereby the second housing, in the second position, is releasably connected to the first housing via the locking arrangement.

3. The coupling device according to claim 1, wherein when a force (F) applied on the third housing connected to the second housing in the second position along the principal axis towards the first position exceeds a predetermined threshold:
the second housing is configured to be released from a connection to the first housing in the second position,
the second housing is configured to be displaced from the second position into the first position, and
the third housing is configured to be released from a connection to the second housing.

4. The coupling device according to claim 1, further comprising a locking mechanism configured to releasably connect the third housing to the second housing.

5. The coupling device according to claim 4, whereby, in the second position of the second housing, the third housing and the second housing are connected by the locking mechanism.

6. The coupling device of claim 4, wherein the third housing comprises a first locking element of the locking mechanism, and the second housing comprises a second locking element of the locking mechanism, wherein the first and second locking elements are configured to releasably lock upon rotation of the first and second locking elements with respect to each other.

7. The coupling device of claim 6, wherein, during a displacement of the second housing and third housing from the first position to the second position, the second locking element is configured to rotate with respect to the first locking element for mating engagement with the first locking element such that the third housing and the second housing are connected in the second position, and during a displacement of the second housing and third housing from the second position to the first position, the second locking element is configured to rotate with respect to the first locking element for disengaging the mating engagement such that the third housing and the second housing are disconnected in the first position.

8. The coupling device according to claim 1, wherein at least one of the first and second sealing elements comprises a resilient membrane.

9. The coupling device according to claim 8, wherein the resilient membrane has a convex shape which is configured to flatten upon abutment of the first sealing element with the second sealing element.

10. The coupling device according to claim 8, wherein the resilient membrane comprises silicone.

11. The coupling device according to claim 1, further comprising an alarm arrangement configured to generate an alarm when the second housing and the third housing are disconnected.

12. The coupling device according to claim 11, wherein the alarm comprises at least one of a visual alarm or an audible alarm.

13. The coupling device according to claim 1, wherein the coupling device is configured to generate a tactile feedback to an operator when the second housing is in the second position.

14. A medical tube for transferring a fluid to or from a patient, wherein the medical tube comprises:
at least one coupling device comprising:
a first housing extending along a principal axis, the first housing comprising a first opening at a back end portion thereof, a second opening at a front end portion thereof, and a tube portion extending from the first opening into the first housing;
a second housing displaceably arranged within the first housing along the principal axis between a first position at the front end portion of the first housing and a second position at the back end portion of the first housing, the second housing comprising a first sealing element; and
a third housing releasably connectable to the second housing and configured for displaceable arrangement within the first housing along the principal axis, the third housing comprising a channel through the third housing, and a second sealing element arranged to seal the channel,
whereby, in the first position of the second housing, the third housing is insertable into the first housing via the second opening thereof, and insertable between the first housing and the first sealing element, such that the first and second sealing elements are configured to abut each other and sealingly separate the tube portion and the channel, and whereby, in the second position of the second housing, the third housing and the second housing are connected and the tube portion projects through the first and second sealing elements for connection with the channel such that a transfer of the fluid through the at least one coupling device is enabled.

15. A medical kit, comprising:
at least one medical tube comprising:
at least one coupling device comprising:
a first housing extending along a principal axis, the first housing comprising a first opening at a back end portion thereof, a second opening at a front end portion thereof, and a tube portion extending from the first opening into the first housing;
a second housing displaceably arranged within the first housing along the principal axis between a first position at the front end portion of the first housing and a second position at the back end portion of the first housing, the second housing comprising a first sealing element; and
a third housing releasably connectable to the second housing and configured for displaceable arrangement within the first housing along the principal axis, the third housing comprising a channel through the third housing, and a second sealing element arranged to seal the channel,
whereby, in the first position of the second housing, the third housing is insertable into the first housing via the second opening thereof, and insertable between the first housing and the first sealing element, such that the first and second sealing elements are configured to abut each other and sealingly separate the tube portion and the channel, and whereby, in the second position of the second housing, the third housing and the second housing are connected and the tube portion projects through the first and second sealing elements for connection with the channel such that a transfer of fluid through the at least one coupling device is enabled,
at least one coupling arrangement provided at at least one end of the at least one medical tube, and
at least one element connected to the medical tube via the at least one coupling arrangement.

* * * * *